US012589016B2

(12) United States Patent
Pohl

(10) Patent No.: US 12,589,016 B2
(45) Date of Patent: Mar. 31, 2026

(54) METHOD FOR SECURING AN ORHOPAEDIC DEVICE AND ORTHOPAEDIC

(71) Applicant: Ottobock SE & Co. KGaA, Duderstadt (DE)

(72) Inventor: Kathrin Pohl, Frankfurt am Main (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 362 days.

(21) Appl. No.: 17/999,889

(22) PCT Filed: May 6, 2021

(86) PCT No.: PCT/EP2021/062078
§ 371 (c)(1),
(2) Date: Nov. 25, 2022

(87) PCT Pub. No.: WO2021/239436
PCT Pub. Date: Dec. 2, 2021

(65) Prior Publication Data
US 2023/0233351 A1     Jul. 27, 2023

(30) Foreign Application Priority Data
May 27, 2020    (DE) ..................... 10 2020 114 185.8

(51) Int. Cl.
A61F 5/01            (2006.01)
(52) U.S. Cl.
CPC ...................................... A61F 5/01 (2013.01)
(58) Field of Classification Search
CPC ... A43C 11/165; A43C 11/20; A43C 11/0078;

A43C 1/00; A43C 1/04; A43C 3/00; A43C 3/16; A43C 3/2071; Y10T 24/21; A61F 5/01; A61F 5/0102; A61F 5/0127; A61F 5/0111; A61F 5/0125; A61F 5/0123; A61F 5/0113; A61F 5/3738; A61F 5/37; A61F 5/3723; A61F 5/0104; A61F 5/02; A61F 5/028; A61F 5/0193; A61F 5/0109; A61F 5/05; A61F 5/373; A61F 5/0118; A61F 5/013; A61F 5/0106; A61F 2250/00;
(Continued)

(56) References Cited

U.S. PATENT DOCUMENTS

| | | | | | |
|---|---|---|---|---|---|
| 783,949 | A | * | 2/1905 | Harden ..................... | A43C 3/00 |
| | | | | | 24/714.4 |
| 3,605,731 | A | * | 9/1971 | Tigges ..................... | F16K 31/02 |
| | | | | | 128/95.1 |

(Continued)

FOREIGN PATENT DOCUMENTS

| | | | | | |
|---|---|---|---|---|---|
| JP | | 3097413 U | * | 1/2004 | |
| WO | WO-2011071522 A1 | * | 6/2011 | ............... | A61F 5/01 |
| WO | 2017191120 A1 | | 11/2017 | | |

*Primary Examiner* — Alireza Nia
*Assistant Examiner* — Michael Milo
(74) *Attorney, Agent, or Firm* — WCF IP

(57) ABSTRACT

A method for securing an orthopaedic device to a body part of a wearer, having a device that includes a base body, from which at least one deflection element with a contact surface protrudes at least one belt and at least one securing element, and included positioning the orthopaedic device on the body part, placing the belt onto the contact surface of the deflection element and fastening the belt on the securing element.

14 Claims, 2 Drawing Sheets

(58) Field of Classification Search
CPC ...... A61F 2005/0167; A61F 2005/0179; A61F
2005/0139; A61F 2005/0174; A61F
2005/0181; A61F 2005/0137; A61F
2005/0144; A44B 11/28; A44B 11/125;
A44B 11/2592; A43B 7/20; A61H
2003/007; A61H 2003/00; A61H 2205/10
USPC ....................................................... 602/5, 62
See application file for complete search history.

(56) References Cited

U.S. PATENT DOCUMENTS

| | | | |
|---|---|---|---|
| 5,743,866 A | | 4/1998 | Bauerfeind et al. |
| 6,119,318 A * | | 9/2000 | Maurer .................... A43C 3/00 |
| | | | 24/713.2 |
| 2007/0239093 A1* | | 10/2007 | Wyatt ................... A61F 5/0118 |
| | | | 602/12 |
| 2013/0139305 A1* | | 6/2013 | Rao ...................... A63B 33/004 |
| | | | 2/452 |
| 2017/0006969 A1* | | 1/2017 | Wang ........................ A41F 1/04 |
| 2019/0083285 A1 | | 3/2019 | Martin |

* cited by examiner

METHOD FOR SECURING AN ORHOPAEDIC DEVICE AND ORTHOPAEDIC

BACKGROUND

Technical Field

The invention generally relates to a method for securing an orthopaedic device to a body part of a wearer.

Description of Related Art

Within the meaning of the present invention, orthopaedic devices refer to particularly to prostheses and orthoses. However, devices intended to support the wearer during strenuous physical work, for example working above one's head, are also considered to be orthopaedic devices.

Such devices are secured to one or multiple body parts. To achieve the necessary stability, support, protective or therapeutic effect, it is often necessary to apply a certain amount of tension to the respective body part on which the device is arranged. For example, this is done using belts that are at least partially placed around the respective body part. Joint orthoses in particular are secured to the respective joint in this way. The belts render it possible to adjust the tension and thus use a single orthosis for different people and wearers of the orthosis without having to produce individual orthoses. The same applies for protheses that feature, for example, a prosthesis socket whose width, i.e. In particular the opening of the prosthesis socket into which the amputation stump is inserted, can be adjusted using a belt.

In this case, an orthopaedic device comprises a base body that is positioned on the respective body part. The orthopaedic device also has at least one belt that is at least partially placed and fastened around the respective body part. To this end, a kind of loop or eyelet made of a plastic or metal is often provided on the base body. The belt has a free end that is passed through this loop or eyelet before being secured on itself, for example. For this purpose, the belt features, for example, a first form-fitting element at its end, such as a Velcro™ element, that can engage with a second, correspondingly designed form-fitting element also arranged on the belt, for example. The two form-fitting elements are then arranged on each other in such a way that it results in a form-fitting connection. Depending on how far the free end of the belt is passed through the loop or eyelet, the width of the belt can be freely adjusted as long as the two form-fitting elements come into contact with each other.

However, it is a disadvantage that the threading of the free end of the belt into the loop or eyelet requires relatively high dexterity, which is not also present in wearers of the orthopaedic device who have limited motor skills. Furthermore, the position of the eyelet or loop depends largely on which body part the orthopaedic device is to be arranged. As such, in addition to the physical restrictions of wearers, it is often difficult to reach the position where the loop or eyelet is located. If the free end of the belt is now to be threaded through the eyelet or loop, the free end must first be inserted, taken hold of with the second hand and pulled through further. This is very difficult, if not impossible, with just one hand.

SUMMARY

The invention therefore aims to propose a method for securing an orthopaedic device to a body part of a wearer that is easy to carry out and still enables individual adjustability and a sufficiently secure connection. The invention also aims to propose a corresponding orthopaedic device.

The invention solves the addressed problem by way of a method for securing an orthopaedic device to a body part of a wearer, the device comprising a base body from which at least one deflection element with a contact surface protrudes, at least one belt and at least one securing element, the method comprising the following steps:

a) positioning the orthopaedic device on the body part, b) placing the belt onto the contact surface of the deflection element and c) securing the belt on the securing element.

The method according to the invention allows the orthopaedic device to be secured to the body part of the wearer without having to thread one end of the belt through a loop or eyelet. As a result, the method is simpler, quicker and easier to perform for people with limited motor skills.

The at least one deflection element protrudes from the base body. In particular, this means that it protrudes in a direction away from the body part of the wearer. The deflection element is, for example, a cylindrical element with a circumferential lateral surface. Part of this lateral surface or the entire lateral surface constitutes the contact surface. It is not essential for the deflection element to have an axis of symmetry or rotation, but it may be advantageous. The deflection element preferably has an edge that limits the contact surface on the side facing away from the base body. The distance of this edge from the base body may vary.

DETAILED DESCRIPTION

Figures 1, 2, 3, 4:
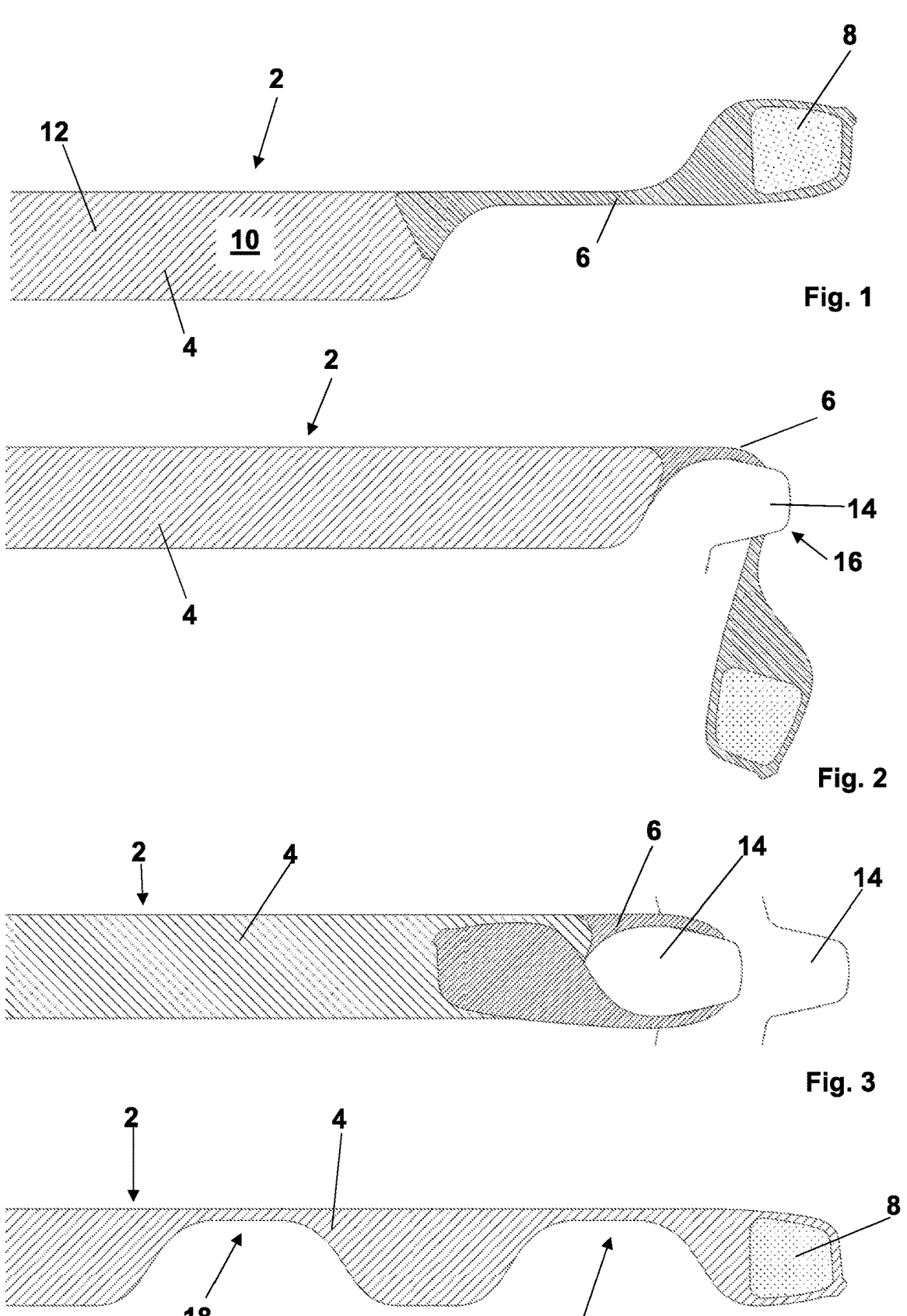
FIG. 1 depicts a belt for an orthopaedic device according to a first embodiment.
FIG. 2 shows the FIG. 1 belt with a textile section and plastic element of the orthopaedic device according to the first embodiment.
FIG. 3 illustrates an orthopaedic device according to the first embodiment in a situation in which an end of the plastic element on which a form-fitting element is located is fixed in the textile section of the belt.
FIG. 4 shows a belt orthopaedic device according to a further embodiment with the plastic element, wherein the textile section extends over its length and the form-fitting element is arranged on the right-hand end.

To perform the method, the orthopaedic device is first arranged on the body part. The wearer then preferably takes a free end of the belt and performs a movement, by way of which the belt is placed on the contact surface of the deflection element. To do so, the belt does not need to be guided through a closed element, such as a loop or an eyelet. The belt also does not have to be passed from one hand to the other. The movement to be performed is preferably a circular movement, by way of which a part of the belt is placed on the contact surface located there via a part of the deflection element. This can be achieved in a simple, quick and secure manner as well as providing the wearer with the possibility to freely adjust the tension to be exerted on the belt via the tensile force he/she is to apply. The belt is subsequently fastened to the securing element.

Furthermore, the design of the orthopaedic device and the method for securing this device according to the invention renders it particularly easy to adjust and, where necessary, change the set tension generated by the tensile force applied. This can be beneficial if, for example, a circumference of the body part to which the orthopaedic device is secured changes throughout the day, for example. Even if the wearer notices after some time that the initial set tension is too great or too small, this can be rectified. To do so, the belt is preferably first released from the securing element. The wearer can then remove the belt from the contact surface of the deflection element and re-position it on the contact surface with a new tension, which may be greater or smaller than the initial tension. The belt is subsequently re-fastened to the securing element. Alternatively or additionally, it is also possible to change the tension without removing the belt from the contact surface of the deflection element. For example, if the tension is not to be increased, the wearer can apply a tensile force after releasing the belt from the securing element which ensures that the belt slides along the contact surface of the deflection element. This increases the tension of the belt. In this state, the belt can be re-fastened on the securing element. Alternatively, the wearer can also reduce the tensile force after releasing the belt from the securing element, thereby ensuring that the belt slides along the contact surface of the deflection element in the opposite direction. As soon as the tension is adjusted to the desired level, the belt can be re-fastened to the securing element.

The belt is preferably made of an elastic material or comprises at least one, but preferably multiple, sections made of an elastic material. Alternatively, the belt is made of elastic material.

In a preferred embodiment, the contact surface has a groove or undercut into which the belt is placed. This ensures that the belt, once placed on the contact surface, cannot slide off or inadvertently become otherwise detached from the deflection element. The belt is situated in the recess of the contact element and can only be removed after the belt has been released from the securing element. The connection is thus more secure, thereby increasing the level of comfort when worn.

The contact surface of the deflection element preferably, although not necessarily, extends over the entire circumference of the deflection element. It is enough to arrange a contact surface in the area of the deflection element that should actually come into contact with the belt. The size of the contact surface, i.e. in particular the size of the area of the circumference of the deflection element over which the contact surface extends, depends largely on the position of the securing element. Moreover, the position in which the end of the belt opposite the free end is arranged on an element of the orthopaedic device, preferably the base body, has an impact on the size and position of the contact surface on the deflection element.

In a preferred embodiment of the invention, the belt is placed on the contact surface in such a way that the belt surrounds the deflection element over at least 25%, preferably at least 40%, especially preferably at least 50%, of its circumference. The larger the section of the contact surface that actually comes into contact with the belt, the larger the surface on which the force transmitted by the belt onto the deflection element is transmitted. This reduces the pressure, so that the orthopaedic device and especially the deflection element can withstand greater forces. This reduces the engineering effort and therefore also the production costs.

Once the orthopaedic device has been secured on the body part of the wearer, the belt extends along two sections. The first section extends from the fixed end of the belt, with which it is secured on a component or element of the orthopaedic device, in particular the base body, to the deflection element. The second section extends from the deflection element to the securing element to which the belt is fastened. The angle between the two sections is decisive for the percentage of the circumference of the deflection element that makes up the contact surface.

In a preferred embodiment, the securing element is arranged on the belt. In this embodiment, the belt is secured on itself when it is fastened to the securing element. In this case, the angle between the two sections is 180°. The contact surface extends across approximately 50% of the circumference of the deflection element. Alternatively or additionally, a securing element t is not arranged on the belt. For example, it may be arranged on another element of the orthopaedic device, for example the base body. In this case, when the belt is fastened, the belt is not secured on itself, so that the angle between the two sections can be greater or smaller than 180°. If the angle is greater than 180°, the two sections of the belt that extend along the two sections cross each other. This is not the case if the angle is smaller than 180°.

With an orthopaedic device according to the invention, the at least one belt usually bridges a gap. In this way, for example, two or more shell elements can be adjusted to one circumference by the at least one belt. However, the gap can also be between the two ends of a single base body, which can be designed in the form of a clasp, for example. In a preferred embodiment, the fixed end of the at least one belt that is not fastened on the securing element is arranged on one side of the gap, while the de-flection element is located on the opposite side of the gap. In particular, in the event that the securing element is arranged on the belt and the belt is thus laid back on it-self when fastened on the securing element, this arrangement means that a force is only applied in a very small area, namely between the securing element on the one side and the deflection element on the other. However, the gap to be bridged often extends across a larger distance, for example along a leg. If a force is to be applied at multiple points or across a larger distance, this can be achieved by using multiple, spaced apart belts, each of which is placed on the contact surface of a deflection element before being fastened on one securing element in order to secure the orthopaedic device. Alternatively or additionally, however, a belt can also be placed around multiple deflection elements, which can be located on the same or different sides of the gap to be bridged.

For example, the belt, which is arranged at its fixed end on one side of the gap to be bridged, can be guided across the gap and placed on the contact surface of a first deflection element. The belt then extends to a second deflection element located on the same side of the gap as the first deflection element. Here, too, the belt is placed on a contact surface of the second deflection element before being fastened to the securing element, which is again located on the opposite side of the gap. In this embodiment, the securing element and the fixed end of the belt are on one side of the gap and the two deflection elements are on the other side of the gap.

In another embodiment, the belt is arranged at its fixed end on one side of the gap to be bridged and is guided across this gap to the first deflection element. There, it is placed on the contact surface of the first deflection element and from there guided to a second deflection element located, however, on the other side of the gap. In this embodiment, once the belt has also been placed on the contact surface of the second deflection element, it is guided again across the gap and thus connected on the opposite side to the securing element located there. In this case, the securing element and the first deflection element are therefore located on one side of the gap and the fixed end of the belt and the second deflection element on the other side of the gap. This results in a zig-zag pattern of the belt across the gap. Of course, combinations of these embodiments are possible, especially with more than two deflection elements, for example three, four or five deflection elements.

Multiple deflection elements can also be provided on one or both sides of the gap, of which only one is used in each case. This can be particularly useful for enabling an adjustability of the applied tension over a larger area. The user than selects the respective relevant deflection element.

The first form-fitting element is arranged on the second form-fitting element such that a form-fitting connection is created. The first form-fitting element is preferably located at a free end of the belt. Alternatively or additionally, the securing element can also be designed for a friction or non-positive connection. For example, the securing element features a slot into which the belt, which preferably has a roughened surface or coating, is inserted and thus clamped. It is also possible for the securing element to be designed in the form of something like a button or mushroom-shaped object that features a section with a smaller diameter and a wider head. The belt can then preferably be placed around the section with the smaller diameter multiple times and thus fastened.

The invention also solves the addressed problem by way of an orthopaedic device for carrying out a method of the type described here. The device has a base body, from which at least one deflection element with a contact surface protrudes, at least one belt and at least one securing element, the belt being arranged and configured to be placed onto the contact surface of the deflection element and fastened to the securing element. Preferably, the belt features a first form-fitting element and the securing element is a correspondingly designed second form-fitting element, so that the first form-fitting element can form a form-fitting connection with the second form-fitting element.

The belt preferably exhibits a width that is reduced in at least one area that can come into contact with the contact surface. In particular, the belt has a circular or almost circular cross-section in this area. Preferably, the cross-section has approximately the same extension in two directions perpendicular to each other This part comes into contact with the contact surface of the deflection element and is placed around the deflection element, so that the belt does not extend in a straight line in this area, but in a curve. This is especially easy to achieve with a cross-section in which the thickness roughly corresponds to the width. Preferably, the belt has multiple such areas, which are preferably separated from each other by at least one area in which the width is not reduced. The user can then roughly set the tension by selecting the reduced width area to be used.

If the belt has a constant or almost constant width, or if the width is significantly greater than the thickness of the belt at this point, even in the area that can come into contact with the contact surface, it is advantageous to rotate the belt when placing it against the contact surface of the deflection element so that the side of the belt that faces the body part of the wearer in other areas of the belt faces the contact surface in the area that can come into contact with the contact surface. For this purpose, a rotation of about 90° can be advantageous.

Preferably, the width in the area that can come into contact with the contact surface is reduced on one side. The belt has two edges that limit the belt at the side. The distance between these two edges is the width of the belt. If the width is constant over the course of the belt, the edges extend parallel to each other. If the width of the belt is now to be reduced in one area, this can be done in different ways. One possibility is the symmetrical reduction of the width. This means that the edges extend towards each other until the desired reduced width is achieved. In the area that is to have the reduced but nevertheless constant width, the edges now run parallel to each other at a smaller distance before they move away from each other again in the further course of the belt to achieve a larger, preferably the original width. As an alternative to the symmetrical reduction of the width, there is also the asymmetrical reduction of the width. This means that both edges do not converge to the same degree. Nevertheless, both edges do extend towards each other, albeit to different extents. In this embodiment too, as soon as the desired distance, i.e. the reduced distance, is achieved, the two edges extend parallel to each other. As the belt progresses, it is advantageous if the edges move away from each other again and the width of the belt increases again. In this case, too, it is advantageous to restore the original width. Looking at the belt from above, it consequently comprises a narrow section which, in the case of symmetrical reduction, is located exactly in the middle of the wider section, while in the case of asymmetrical reduction it is not central.

Another option is one-sided reduction. Here, only one of the two edges extends to-wards the other, while the second edge continues to extend in a straight line. The narrower section is therefore located at the edge of the original wider section. This embodiment is preferred, with the narrower section of the belt being particularly preferred on the side of the belt facing away from the deflection element. Therefore, if the belt is placed around the deflection element in such a way that, starting from its fixed end and moving towards the first form-fitting element, it forms a right-hand curve, the narrower section is located at the left edge of the belt. If, however, the belt is placed around the deflection element in such a way that, starting from its fixed end and moving towards the first form-fitting element, it forms a left-hand curve, the narrower section is located at the right edge of the belt. If the orthopaedic device comprises multiple deflection elements, it is advantageous for the belt to also comprise multiple areas with a reduced width. Particularly preferably, the one-sided reduction in width is used in each of these areas, with the narrower section located on the right or left edge of the belt, depending on whether the belt forms a left-hand curve or a right-hand curve around the deflection element.

The area with reduced width is preferably longer than a contact area of the belt via which the belt comes into contact with the contact surface. Preferably, the area with reduced width is at least 1 cm, especially preferably at least 2 cm, longer This allows the tension to be adjusted very finely and almost infinitely; especially preferably, it can be infinitely adjusted.

The belt preferably features multiple areas with reduced width. The user can then select which of these areas he/she places around the deflection element, thereby varying the tension across a larger area. He/she first roughly selects the area in which the applied tension should be located by selecting the section with reduced width that comes into contact with the deflection element. He/she can subsequently conduct a fine adjustment as described above.

In a preferred embodiment, this area is formed by a plastic element, especially an injection-molded part. It has the required stability and tensile strength, and is preferably stuck, sewn or welded to other sections of the belt. The other sections of the belt are preferably made of a textile and are connected to the plastic element.

The belt preferably features a textile section on which the plastic element is arranged. Particularly preferably, the plastic element forms a free end of the belt. Specifically, this means that there is a textile section on only one side of the plastic element. If the belt has a form-fitting element, it is preferably arranged on the plastic element.

The orthopaedic device preferably has at least two, preferably at least three or four, deflection elements, each of which comprises a contact surface and protrudes above the base body. This allows the above-mentioned embodiments to be realized and the force curve to be produced by the belt to be adjusted almost without limit.

In an especially preferred embodiment, the at least one deflection element is designed in the form of a hook.

In the following, a number of embodiment examples of the invention will be explained in more detail with the aid of the accompanying drawings. They show FIGS. 1 to 3—a section of an orthopaedic device according to a first embodiment of the present invention, FIG. 4—a section of an orthopaedic device according to a further embodiment of the present invention, and FIG. 5—an orthopaedic device according to the first embodiment combined with an example prosthetic socket as one example base body.

FIG. 1 depicts a belt 2 for an orthopaedic device according to an embodiment example of the present invention. It comprises a textile section 4 and a plastic element 6 that is arranged at one end of the textile section 4. A first form-fitting element 8 is arranged at one end of the plastic element 6—in FIG. 1 the right-hand end-which simultaneously forms the right-hand end of the belt 2. The textile section 4 forms a second form-fitting element 10 and thus the securing element 12 to which the belt 2 is fastened.

FIG. 2 shows the belt 2 with the textile section 4 and the plastic element 6. The plastic element 6 has already been partially placed around a deflection element 14. The deflection element 14 features an undercut 16 into which the plastic element 6 with the area of reduced width is inserted.

FIG. 3 shows the situation in which the end of the plastic element 6, on which the first form-fitting element 8 is located, is fixed on the textile section 4 of the belt 2. The plastic element 6 and thus the belt 2 at least partially surround the deflection element 14. The undercut 16, into which the belt 2 with the plastic element 6 is inserted, prevents the belt 2 from being able to slide off of the deflection element 14, thereby releasing the connection. FIG. 3 also depicts a second deflection element 14 around which the plastic element 6 of the belt 2 could have also been placed. As a result, the orthopaedic device would have been secured under greater tension on a body part of the wearer of the orthopaedic device that is not shown.

FIG. 4 shows a belt 2 without the plastic element 6. The textile section 4 extends over the entire length. In FIG. 4, the form-fitting element 8 is arranged at the right-hand end. Unlike the belt 2 in FIGS. 1 to 3, the belt 2 in FIG. 4 has two areas 18 in which the width of the belt 2 is reduced. It is a one-sided reduction, as the reduction has only taken place on the lower side of the belt in FIG. 4. The belt 2 can be placed in different positions around a deflection element 14. Each of the two areas 18 can come into contact with the deflection element 14, thereby enabling the adjustment of the tension under which the orthopaedic device—of which the belt 2 is a part—is arranged on a body part of the wearer.

8

Figure 5:
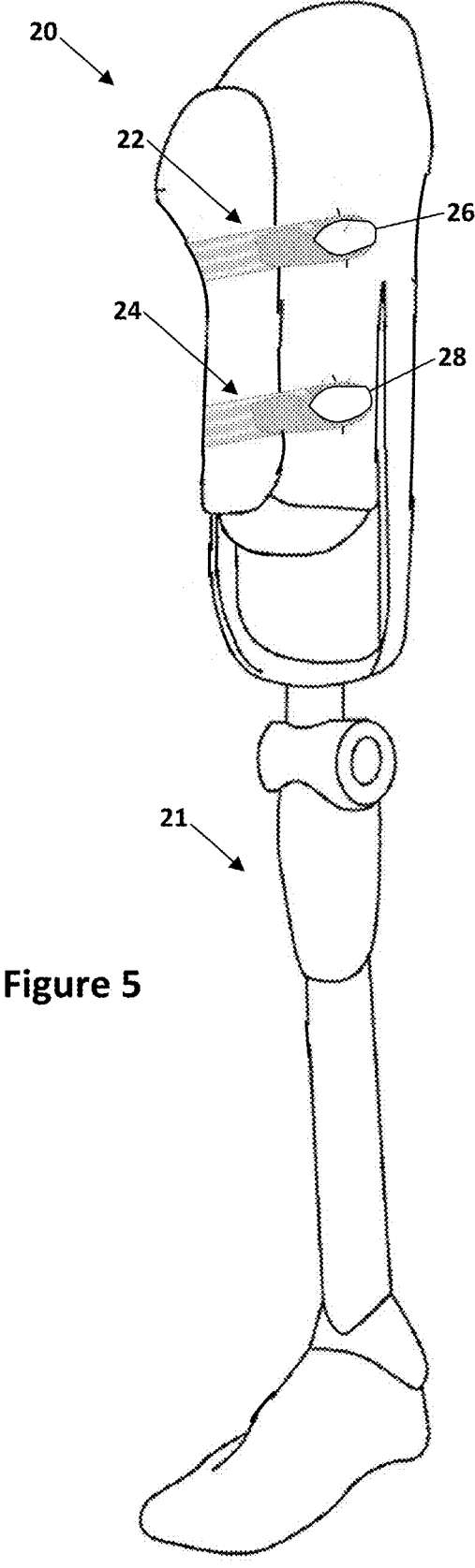
FIG. 5 shows an orthopaedic device according to the first embodiment combined with an example prosthetic socket as one example base body.

FIG. 5 shows a combination of an orthopaedic device 20 combined with an example prosthetic socket 22 including, as an example base body, a first belt 22 having an area in which the width is reduced wrapped around a first deflection element 26 and a second belt 24 having an area in which the width is reduced wrapped around a second deflection element 28, the first and second deflection elements 26 and 28 also attached to the prosthetic socket.

REFERENCE LIST 2 belt
4 textile section
6 plastic element
8 first form-fitting element
10 second form-fitting element
12 securing element
14 deflection element
16 undercut
18 area
20 orthopaedic device according to the first embodiment combined with prosthetic socket as one example base body
22 first belt
24 second belt
26 first deflection element
28 second deflection element

The invention claimed is:

1. A method for securing an orthopaedic device to a body part of a wearer, wherein the orthopaedic device comprises:
a base body,
at least one belt, extending from a fixed end to an opposite end, the fixed end that is secured to the base body or to another structure of the orthopaedic device,
at least one deflection element, comprising a contact surface protruding from the base body away from the body part of the wearer when the body part is positioned in the orthopaedic device and extending in a longitudinal direction,
at least one securing element, arranged on the at least one belt configured to releasably fasten the at least one belt on the at least one securing element,
wherein the method for securing the orthopaedic device comprises:
positioning the orthopaedic device on the body part of the wearer,
placing the at least one belt onto the contact surface of the at least one deflection element, and
fastening the at least one belt on the at least one securing element,
wherein, when the method for securing the orthopaedic device is configured such that when completed, the at least one belt has a first section that extends from the fixed end of the at least one belt to the deflection element, and has a second section that extends from the deflection element to the at least one securing element on which the belt is fastened,
wherein the contact surface comprises a groove or undercut in which the at least one belt is placed, and wherein the groove or undercut is transverse to the longitudinal direction of the at least one deflection element,
wherein the at least one deflection element has a center portion between two spaced apart edges,
wherein the at least one belt first extends in a same longitudinal direction as the longitudinal direction of the at least one deflection element, and is then wrapped under the center portion and around the two spaced apart edges and is secured to the at least one securing element on the at least one belt.

2. An orthopaedic device for carrying out the method according to claim 1, comprising:

a base body, at least one belt, extending from a fixed end to an opposite end, the fixed end that is secured to the base body or to another structure of the orthopaedic device, at least one deflection element with a contact surface, wherein the at least one deflection element protrudes from the base body, and at least one securing element, arranged on the at least one belt or on another structure of the orthopaedic device and configured to releasably fasten the at least one belt on the at least one securing element, wherein the at least one belt is arranged and configured to be placed onto the contact surface of the at least one deflection element and fastened on to the at least one securing element, and when the orthopaedic device is placed onto contact surface and the at least one belt is fastened on the at least one securing element, the at least one belt has a first section that extends from the fixed end of the at least one belt to the deflection element, and has a second section that extends from the deflection element to the at least one securing element on which the belt is fastened.

3. The orthopaedic device according to claim 2, wherein the at least one belt has a width and at least one area of the at least one belt has a reduced width, and the at least one area is configured to come into contact with the contact surface.

4. The orthopaedic device according to claim 3, wherein the at least one area of the at least one belt comprises a plastic element.

5. The orthopaedic device according to claim 4, wherein the at least one belt comprises a textile section on which the plastic element is arranged.

6. The orthopaedic device according to claim 5 wherein the plastic element forms a free end of the at least one belt.

7. The orthopaedic device according to claim 3, wherein the at least one area having the reduced width is longer than a contact area of the at least one belt via which the at least one belt comes into contact with the contact surface.

8. The orthopaedic device according to claim 7 wherein the at least one area is at least 1 cm longer than the contact area of the at least one belt.

9. The orthopaedic device according to claim 3, wherein the reduced width comprises, in the at least one area, a reduction of the width of the belt on one side.

10. The orthopaedic device according to claim 2, wherein the at least one deflection element comprises a plurality of deflection elements, each with a contact surface, protruding away from the base body.

11. The orthopaedic device according to claim 2, wherein the at least one deflection element is configured in a form of a hook.

12. The method according to claim 1, wherein the groove or undercut has a circumference, and the at least one belt is placed on the contact surface so that the at least one belt surrounds the at least one deflection element over at least 25% of said circumference.

13. The method according to claim 1, wherein the at least one securing element is arranged on the at least one belt.

14. The method according to claim 1, wherein the at least one belt comprises a first form-fitting element and the at least one securing element comprises a second form-fitting element, wherein fastening the at least one belt on the at least one securing element comprises engaging the first form-fitting element and the second form-fitting element so as to create a form-fitting connection.

* * * * *